United States Patent [19]
Long et al.

[11] Patent Number: 5,507,742
[45] Date of Patent: Apr. 16, 1996

[54] MULTIFUNCTION LASER-POWERED SURGICAL TOOL WITH OPTICAL ELECTROCAUTERY CAPABILITY

[75] Inventors: Gary Long; David Eyman, both of Cincinnati, Ohio; Jayna McIntrye, Tulsa, Okla.

[73] Assignee: Laser Centers of America, Cincinnati, Ohio

[21] Appl. No.: 161,373

[22] Filed: Dec. 2, 1993

[51] Int. Cl.⁶ ........................... A61B 17/36
[52] U.S. Cl. .............. 606/15; 606/13; 606/27; 606/16
[58] Field of Search .................. 606/7, 15, 16, 606/17, 10, 13, 27, 28, 1; 607/88, 89

[56] References Cited

U.S. PATENT DOCUMENTS

| | | | |
|---|---|---|---|
| 4,249,533 | 2/1981 | Komiya | 606/15 |
| 4,662,368 | 5/1987 | Hussein et al. | |
| 4,773,413 | 9/1988 | Hussein et al. | 606/7 |
| 4,848,339 | 7/1989 | Rink et al. | |
| 4,943,290 | 7/1990 | Rexroth et al. | |
| 4,950,267 | 8/1990 | Ishihara et al. | |
| 5,029,588 | 7/1991 | Yock et al. | 606/7 X |
| 5,071,222 | 12/1991 | Laakmann et al. | 606/28 X |
| 5,080,660 | 1/1992 | Buelna | |
| 5,100,402 | 3/1992 | Fan | |
| 5,114,422 | 5/1992 | Cosmescu | |
| 5,147,354 | 9/1992 | Boutacoff et al. | |
| 5,158,561 | 10/1992 | Rydell et al. | |
| 5,163,935 | 11/1992 | Black et al. | |
| 5,164,945 | 11/1992 | Long et al. | |
| 5,186,714 | 2/1993 | Boudreault et al. | |
| 5,195,541 | 3/1993 | Obenchain | |
| 5,195,958 | 3/1993 | Phillips | |
| 5,290,299 | 3/1994 | Fain et al. | 606/1 X |
| 5,314,424 | 5/1994 | Nicholas | 606/1 X |

*Primary Examiner*—Stephen C. Pellegrino
*Assistant Examiner*—Michael Peffley
*Attorney, Agent, or Firm*—Lowe, Price, Leblanc & Becker

[57] ABSTRACT

An endoscopic tool has an elongate cylindrical cannula with an open hooked end insertable into the body of a patient with a trocar element providing a laser powered flux of energy for precise incision and optional cauterization of tissue. A conventional pointed trocar may be used with the hooked cannula to permit forcible insertion of the hooked cannula end to the selected surgical site. In the alternative, a laser energy conveying trocar may be used with the hooked cannula or homeostatic insertion into the patient's body. The active distal end portion of the trocar may be provided with a selectively shaped energy-delivering tip element. The energy-delivering tip element may be provided with a sub-surface heating region in which a selected implanted material converts received laser energy into heat for application to tissue held in the hooked open end portion of the cannula. Once the selected tissue is hooked, the surgeon may forcibly apply the heated or laser-energy emitting surface of the tip element to the tissue to be vaporized and incised. A cauterizing surface may be provided on the tip element of the trocar or, in the alternative to the hooked portion of the cannula.

19 Claims, 6 Drawing Sheets

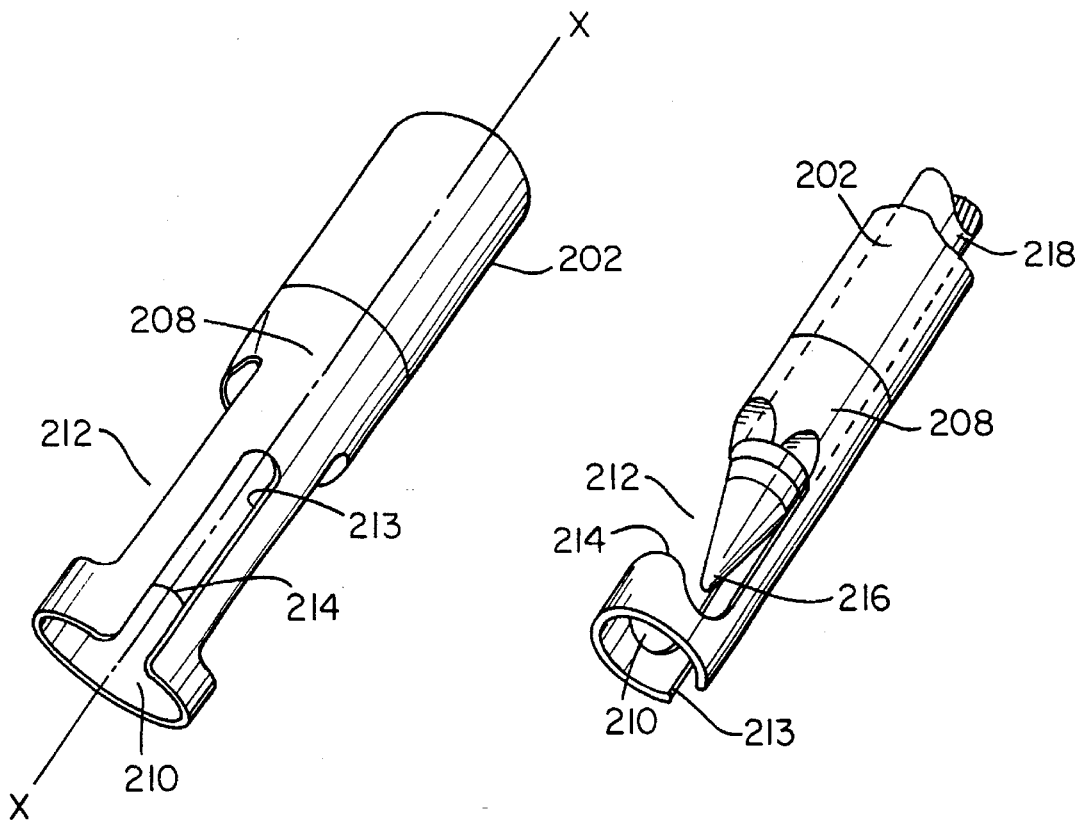
Figure 6
Figure 7
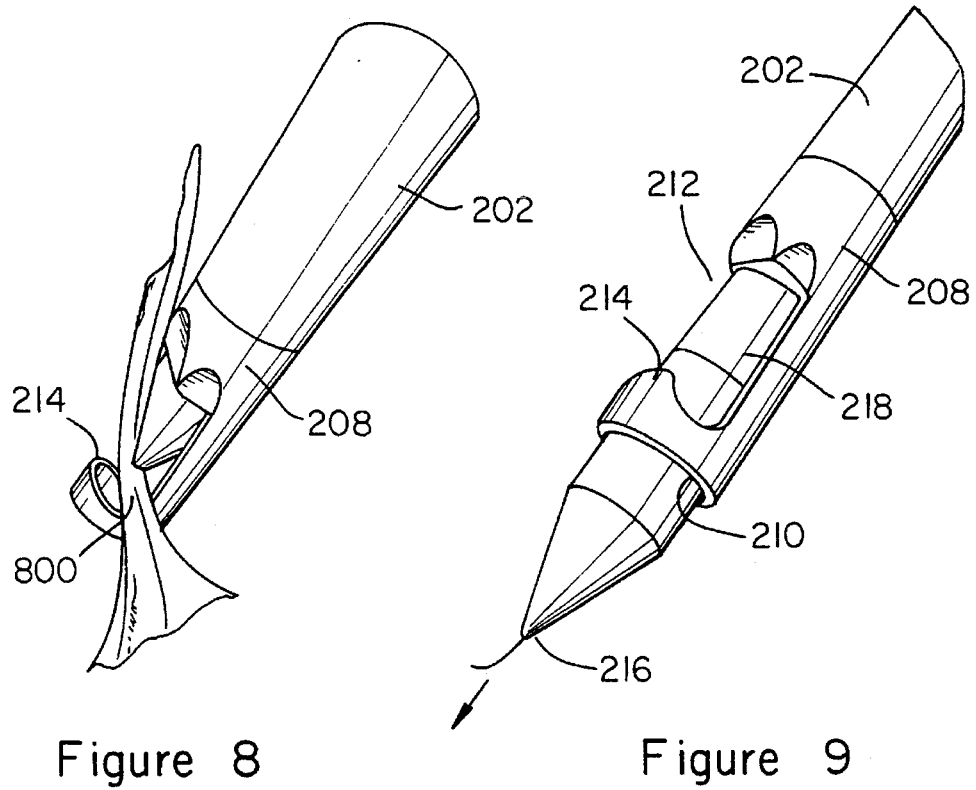
Figure 8
Figure 9

MULTIFUNCTION LASER-POWERED SURGICAL TOOL WITH OPTICAL ELECTROCAUTERY CAPABILITY

FIELD OF THE INVENTION

This invention relates to apparatus for performing surgical incisions and body-fluid coagulations at precisely selected locations through a cannula inserted into a patient's body, and more particularly to a durable, multi-function, laser energy powered, small-bore, precision surgical tool insertable through conventional cannulae for internal surgery.

BACKGROUND OF THE PRIOR ART

There are many circumstances in which it is undesirable for a surgeon to make a relatively large incision in a patient's body in order to perform surgical procedures at internal locations. With wide availability of fiber-optic techniques, surgeons can now avoid making large abdominal incisions by using endoscopic surgical techniques. This typically requires the surgeon to forcibly introduce, under local anesthetic, one or more cannulae through the outer skin into the patient's body. Such cannulae typically have outer diameters in the range 5–10 mm.

As best understood with reference to FIG. 1, a sharp-pointed rod, known as a "trocar", is provided inside the cannula and facilitates forcible intromission of the cannula into the patient's body. The trocar with its point projecting at the front of the cannula is thus used to perforate the outer skin and enables pushing in of the elongate cannula (with the elongate body of the trocar within) through a succession of skin, muscle and fat layers, e.g., for laparoscopic surgery in the abdomen of a patient. Following such an insertion of the trocar and its surrounding cannula, the trocar is removed and the cannula left in place. The surgeon can thereafter insert through the cannula a variety of small bore instrumentation as necessary to perform various surgical functions. It is quite common to employ a number of cannulae suitably placed, as determined by x-ray or ultrasonic scanning of the patient's body, so that the innermost ends of the various cannulae are disposed close to the selected surgical site.

The variety of instruments which may thus be deployed through one or more cannulae include an optic fiber connected to finely-controlled camera equipment to view and externally display the surgical field on a monitor for study by the surgical team, instruments for specifically grasping and/or manipulating tissue, or a multi-function device by which the surgeon can perform cutting and body-fluid coagulating functions simultaneously. The active end portion of such a device may be a laser energy heated element or a laser-energy emitting tip element.

Through endoscopy surgeons can perform very precise surgery by remote control of the surgical tools. The key to success is precisely adjustable placement of the cannulae at suitable locations and in specific orientation with respect to the surgical site, so that instruments may be introduced through the cannulae selectively. Thus, for example, the surgeon most likely will place a cannula which is to be used to obtain a view of the surgical field via fiber optics above the surgical site rather than to a side thereof. As indicated earlier, during a complex surgical procedure the surgical team may remove an instrument from a particular cannula and replace it with another instrument and/or move the removed instrument into another cannula. If this technique is to be practiced, depending on how more than one instrument is to be used, there may be difficulties associated with the location of the available cannulae. This is particularly serious when very precise surgical operations are to be performed and particularly where it is essential to minimize internal trauma to the patient in the course of performing the surgery.

The present invention is intended to afford a surgeon greater latitude and efficiency in precisely performing a variety of surgical functions through one or more cannulae.

SUMMARY OF THE INVENTION

It is a principal object of the present invention to provide a multi-function surgical tool that may be precisely deployed and utilized through a hook-ended cannula positioned to engage selected tissue in a patient's body.

Another object of this invention is to facilitate endoscopic surgery by provision of laser energy through a hook-ended cannula positioned selectively about a surgical site in a patient's body.

A further object of this invention is to provide a sturdy and reusable surgical tool for utilizing laser energy to perform multiple functions, such as incision, coagulation and electrocautery, in endoscopic surgery.

An even further object of this invention is to provide a laser-energy powered surgical tool that may be used in conjunction with cooperating devices deployed via conventional cannulae to perform a variety of surgical functions by applying a laser energy heated element at precisely selected locations inside a patient's body, with an optional electrocautery function.

Yet another related object of this invention is to provide a method of incising precisely held selected tissue, located in a confined region, by applying laser-powered energy at a high temperature to vaporize, and optionally cauterize, the tissue.

These and other related objects are realized by providing a multifunction surgical tool for applying a flow of laser-powered energy to selected tissue precisely held in a patient's body, the tool including a cannula and a trocar. In the preferred embodiment, the cannula includes an elongate hollow cylindrical body and has a first connector part at a first end, and a hollow, open, hooked element at a second end. Upon placement of the cannula with its second end inside the patient's body, the surgeon can hook selected tissue with the open hooked element. The trocar includes an elongate element slidably inserted inside the hollow body of the cannula, and has a second connector part at a connectable end for connection with the first connector part of the cannula in a manner which permits slidable motion between the first and second connector parts as well as between the trocar and the cannula. The elongate element of the trocar has a distal end for delivery of a flow of laser-powered energy therethrough to the tissue hooked by the hooked element.

In a related aspect of this invention, there is provided a method for performing surgical operations on selected tissue at a confined internal site in a patient's body, including the steps of:

providing an elongate tubular cannula having a first connector part at an outside end and an open, hollow, hooked portion at a distal end with the hooked portion engaging the selected tissue;

providing an elongate laser-energy transmitting trocar through the tubular cannula, with the trocar having a second connector at an outside end slidably connected with the first connector and with an energy-delivering tip element at a distal end of the trocar located in the open hooked portion of the cannula;

slidably moving the tip element relative to the hooked portion, by slidably moving the first and second connector parts relative to each other outside the patient's body, until an energy-delivering surface of the tip element contacts the engaged tissue; and providing a controlled flow of energy to the tip element to heat said engaged tissue contacted thereby.

BRIEF DESCRIPTION OF THE DRAWING

FIG. 6 is an enlarged perspective view of the distal end hook structure of the cannula according to the preferred embodiment per FIGS. 2 and 3.

FIG. 7 is an enlarged perspective view of the distal end portion of the preferred embodiment with the extreme distal pointed end of a laser energy delivering element retracted within a distal end hook structure surrounding the same.

FIG. 8 is a schematic perspective view to explain how a portion of body tissue may be hooked at the distal end of the preferred embodiment for application of laser energy to incise such tissue.

FIG. 9 is a partial perspective view of the distal end portion of the preferred embodiment, to illustrate a manner in which a laser energy delivering tip portion may be extended beyond the surrounding hook portion.

DETAILED DESCRIPTION OF THE PREFERRED EMBODIMENTS

Figure 1:
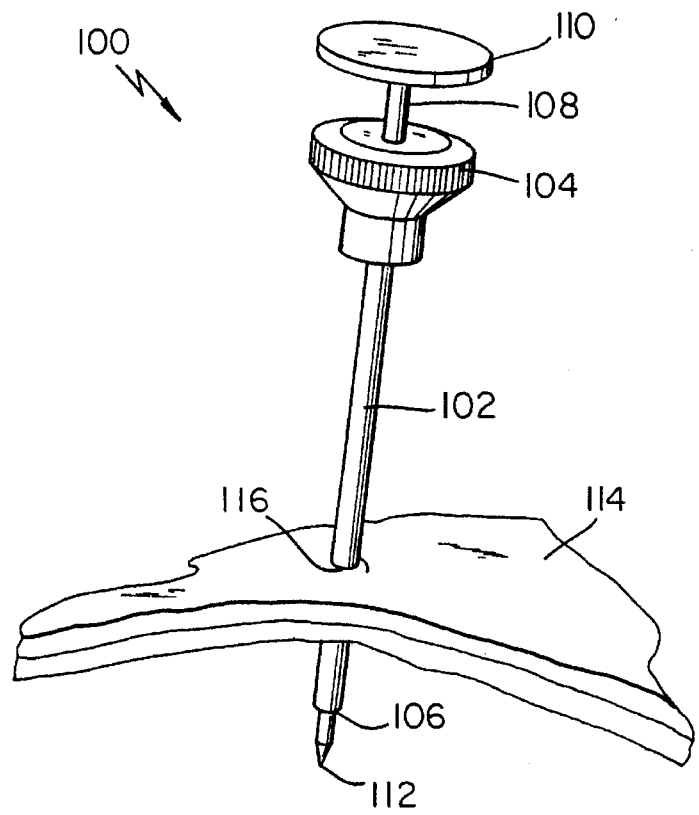
FIG. 1 is a schematic perspective view to explain the manner in which a conventional cannula, with a trocar therein disposed, may be inserted through outer layers of skin, fat and muscle into a patient's body.

Surgical instruments comprising a thin-walled cylindrical cannula and an elongate rod-like trocar inserted therethrough are well know. As indicated in FIG. 1, such a known endoscopic surgical instrument 100 typically has an elongate cannula 102 with a user-graspable head element 104 at an outer end, and a square-cut smooth-edged, circular opening at a distal end 106 which is disposed inside the patient's body during use. The trocar has an elongate, generally solid body 108 having an external diameter such as to permit a closed sliding fit inside the hollow body of cannula 102, and a length which exceeds that of the cannula 102. At an outside end of trocar 108 is a user-contactable head 110, and at a distal end of the elongate portion of trocar 108, extending past opening 106 of cannula 102, is a pointed end 112. Head 104 of such a conventional surgical instrument may be provided with a mechanism for securely locking-onto trocar 108 with point 112 of the trocar located just outside of opening 106 of cannula 102. In this disposition, by the application of a force to head 110 of trocar 108, the surgeon can penetrate through, for example, the abdominal wall of the patient to locate the cannula opening 106 at a desired location. This is one preliminary aspect of what is generally known as "laparoscopic" surgery, but the same general principle applies in any kind of endoscopic surgical procedure.

Following the above-described insertion of the cooperating combination of cannula 102 and trocar 108, following release of any connection therebetween by operation of any securing means (not shown) in cannula head 104, a pulling force may be applied to trocar head 110 to extract it totally out of cannula 102. The surgeon now has access through the very small puncture 116 in the patient's body to the tissues immediately in front of and/or around cannula opening 106.

The surgeon may, thereafter, insert a conventional optic fiber element to enable visual inspection of the tissue in front of and around cannula opening 106, and may then follow it up by inserting a biopsy-obtaining element through cannula 102 or insert any known conventional small-bored, surgical tool to perform a specific surgical operation on such tissue.

As persons of ordinary skill in the surgical arts will appreciate, when working at a confined site, e.g., at a knee joint or within the cranial cavity of a patient, uncontrolled application of energy, e.g., by a conventional laser-energy applying tool inserted through cannula 102, does not permit the making of precise incisions at a controlled rate. It is this precision which is provided by the preferred embodiment of the present invention as illustrated in FIG. 2.

Figure 2:
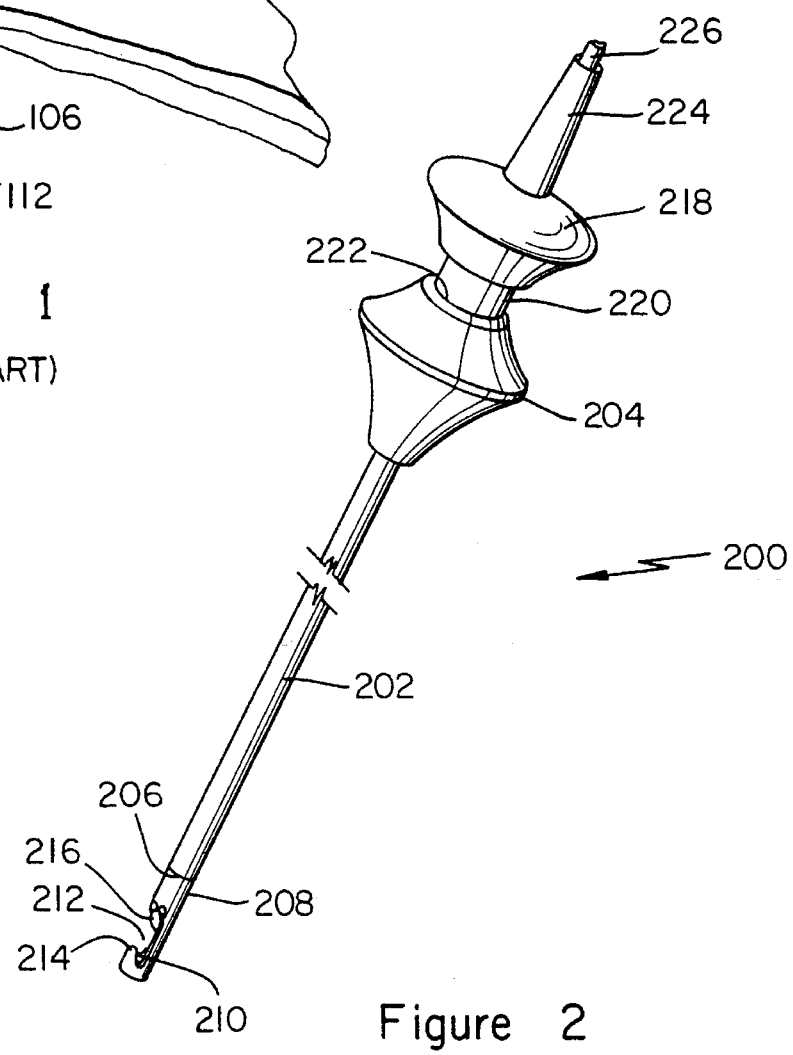
FIG. 2 is a perspective view of a surgical tool according to a preferred embodiment of this invention.

Referring to FIG. 2, a laser-powered surgical tool 200 according to a preferred embodiment of this invention includes an elongate tubular cannula body 202 provided at one end with a front handle section 204 and at a distal end 206 with a hollow, open, hooked element 208. This hooked element 208 has a generally cylindrical body open at a distal end 210 and a cutout 212 formed to leave a hook lip 214 very close to the open end thereof.

Through the hollow front handle section 204 and the tubular body of cannula 202 there is inserted a laser member body having a specifically shaped distal end 216 and a second end at which is provided a back handle section 218 comprising a cylindrical connector portion 220 shaped and sized to be slidably insertable into a corresponding opening 222 of front handle section 204 for engagement therein as described more fully hereinbelow. Back handle section 218 is formed to receive a stress-relief member 224 by which, for example, a conventional optic fiber/cable 226 receives laser energy flux from a laser source (not shown) for conveyance through the length of the trocar for transmission therethrough to tip 216. Cable 226, in known manner, may be formed to include electrical wires to convey a cauterizing current to distal end 216, as described below.

Figures 3, 4:
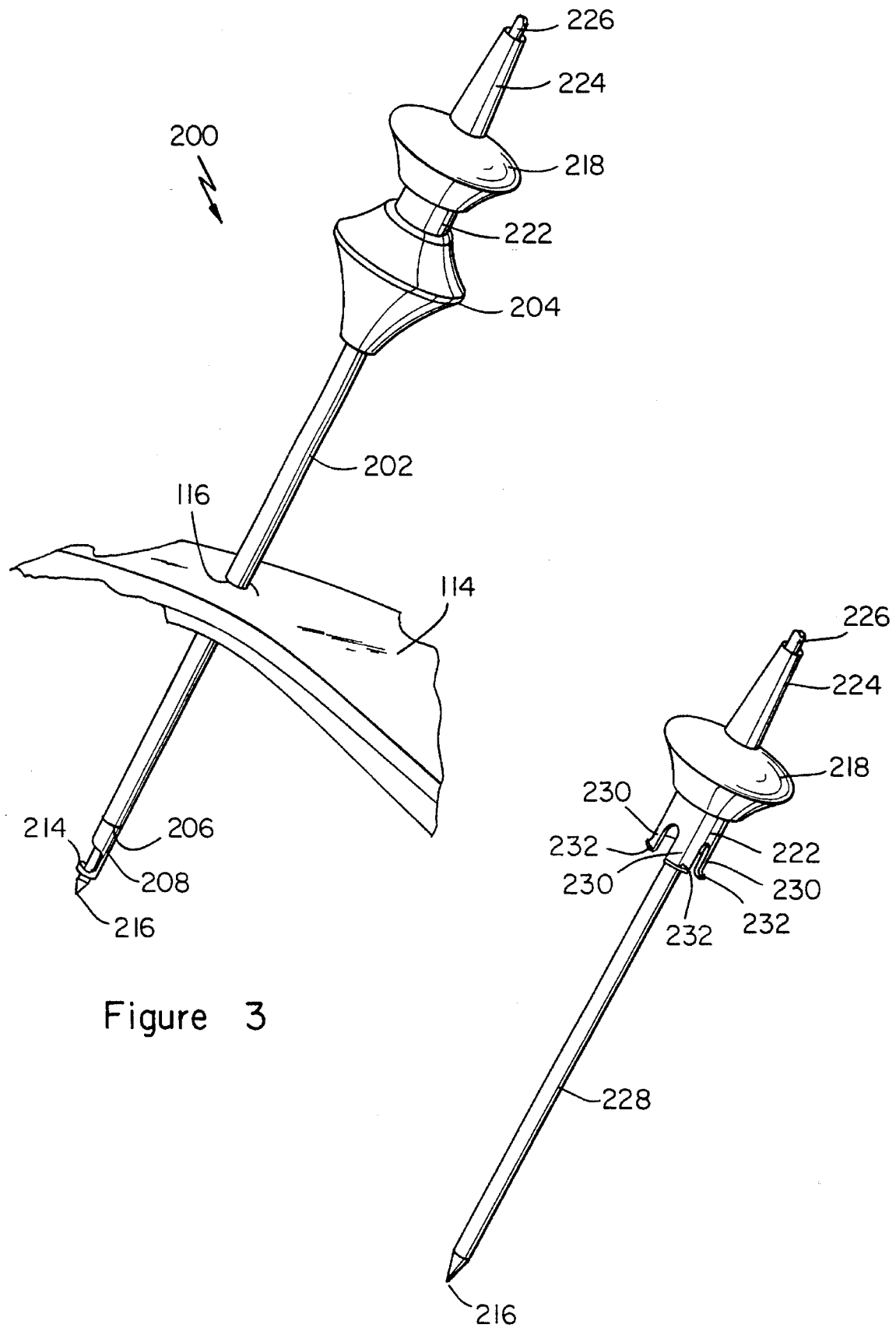
FIG. 3 is a schematic perspective view, generally comparable to FIG. 1, to illustrate the disposition of the preferred embodiment per FIG. 2 through outer layers of skin and muscle into a portion of a patient's body.
FIG. 4 is a perspective view of a one-piece spring-loaded laser energy delivering element shaped and sized to replace a trocar after a cannula has been located into patient's body.

As generally indicated in FIG. 3, the combination of cannula 202 and laser member 228 extending therethrough can be used as a trocar to puncture through an outer body wall or tissue, for example, the abdominal wall 114 of a patient through the same type of puncture 116 as discussed with reference to the known surgical tool 100 per FIG. 1. Thus, the intromission of the hollow, open, hooked element 208 at the distal end of cannula 202 very close to the tissue to be surgically operated upon is readily accomplished in known manner.

The surgeon may use a conventional fiber-optic viewing element of a length and diameter comparable to trocar 228, inserted through hook-ended cannula 202.

Laser member 228, as best seen in FIG. 4, has a lower cylindrical portion 222 which serves as a connector element. This cylindrical portion 222 has a plurality of cutouts which define a corresponding plurality of resiliently flexible but relatively stiff connector legs 230 each having an outward lip 232 at a distal edge.

Figure 5:
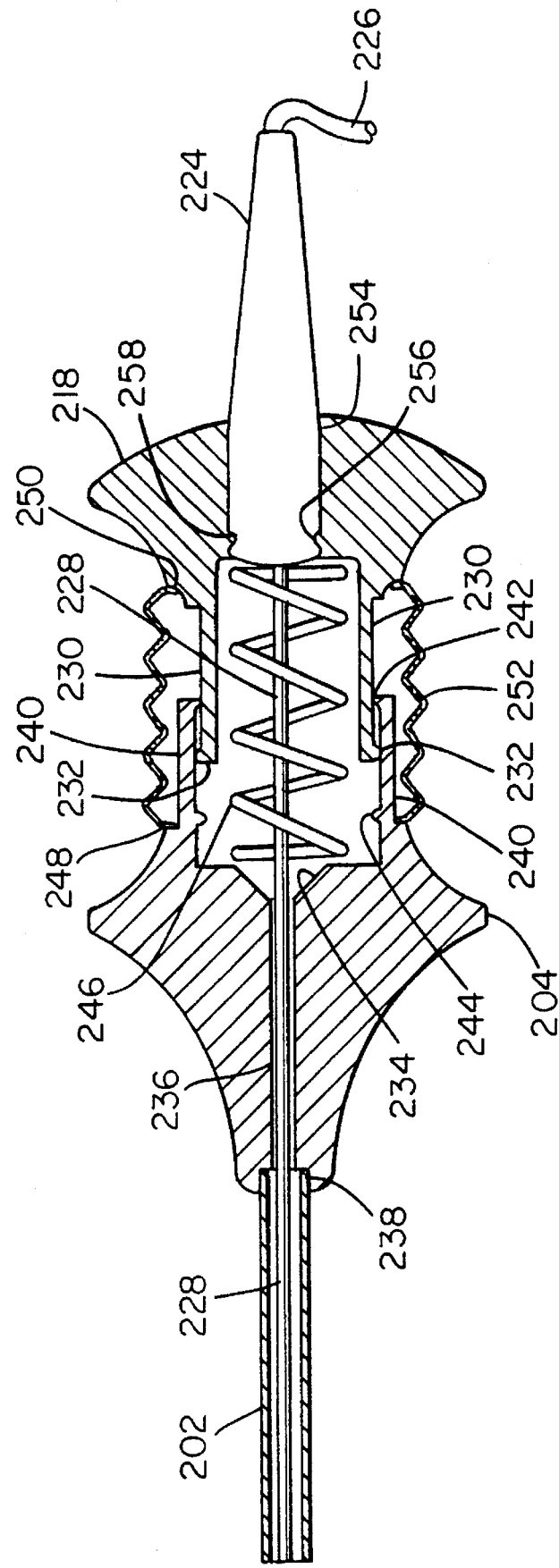
FIG. 5 is a longitudinal cross-sectional view, according to the preferred embodiment, of a junction between the two handle sections.

As best seen in the longitudinal cross-sectional view per FIG. 5, at the inside center of front handle section 204 there is provided a conical recess 234 communicating with a central bore 236 which is coaxial with a tubular body of cannula 202. This recess 234 prevents damage to the tip when the laser member 228 is introduced into cannula 202. Front handle section 204 is attached to this tubular body at a second recess 238 by adhesion with a suitable adhesive or by any other suitable known means.

As will be appreciated, the provision of conical recess 234 also facilitates centering of the laser member 228 inserted through central bore 236 of front handle section 204. Front handle section 204 also has a distal central cylindrical connector portion 240 which is generally similar to the trocar connector portion 222 but has a somewhat larger diameter to receive legs 230 thereof as shown in FIG. 5. The cannula connector portion 240 is cylindrical, i.e., lacks the types of cutouts which define legs 230 in trocar connector portion 222, and has a radially inward lip 242. Also, at the inside cylindrical surface of cannula connector portion 240 there is provided a radially inward annular ridge 244 which holds the back handle section in place forward extending the laser tip beyond the hook (FIG. 9) for use as a standard laser tip.

In the preferred embodiment, there is provided a compressible resilient helical spring 246 which is sized to be in predetermined compression within the limits of slidable movement permitted between cannula 202 and laser member 228 at all times when the aforementioned elements are assembled as illustrated in FIG. 5. Spring 246 thus ensures that there is a continual biasing force tending to drive back handle section 218 axially away from front handle section 204 and, comensurately, to drive the distal end 216 of trocar 228 into a non-exposed position within either the unrelieved cylindrical portion of the open, hooked end element 208 or end 206 of cannula 202.

Between corresponding cannula shoulders 248 and 250, respectively defined in front handle section 204 and back handle section 218, there is provided an accordion-type, resilient, generally cylindrical sealing element 252 which prevents the ingress of ambient dirt and body fluids into the space immediately surrounding laser member 228 and in the annular cylindrical space defined between the outer cylindrical surface of laser member 228 and the inner cylindrical surface of cannula 202. This sealing element 252 also serves to retain within the assembled elements any body fluids that may seep through cannula 202 as laser member 228 is moved into, along, and out of the interior of cannula 202. Note that the above-described elements, as assembled per FIGS. 1–5, permit not only relative sliding movement between cannula 202 and laser member 228 but also allow relative rotational motion between them and between them respective front and back handle sections 204 and 218.

Stress-relief element 224 at the end of optic fiber 226 fits into a central bore 254 defined within back handle section 218. Near the inner end of stress-relief element 224 there may be provided one or more recesses 256 within which extend corresponding protrusions 258 formed within bore 254. Coaction between recesses 256 and corresponding positioned protrusions 258 ensures detachable attachment between stress-relief element 224 and back handle section 218. Such releasable attachment facilitates physical separation and cleansing/sterilization of the various elements, as most appropriate in light of the materials from which the various elements are made. Sealing element 252 may be adhered to either one or both of front handle section 204 or back handle section 218 at their corresponding shoulders 248 or 250, respectively, with any suitable known adhesive.

As best seen in FIG. 6, hooked element 208 is affixed concentrically and coaxially with respect to a longitudinal X—X of cannula 202, and has an open and preferably circular open end 210. A side cutout 212 is shaped to generate a hooked lip 214 very close to the open end 210. In addition, an elongate longitudinal second cutout 213 is provided in a longitudinal direction inwardly of open end 210 for visualization of the laser tip. Care is taken to ensure that there are no sharp or ragged edges which could unintentionally snag any tissue in the patient.

As will be readily appreciated, a user handling the device during use will grasp the front and back handle sections 204 and 218, respectively, together and will manipulate them, either together or relative to each other, as necessary to hook selected tissue and to operate thereon. The structure internal to the front and back handle sections 204 and 218 serves as a releasable connector between them. Obvious modifications can no doubt be made to the exemplary preferred embodiment for performing this function.

As best seen in FIG. 7 in a somewhat enlarged view of the distal end of the assembly per FIG. 2, a shaped point 216 of a laser member 228 can be located within and very close to the hooked lip 214, controlled by the amount of pressure applied by the user/surgeon to back handle section 218 with respect to front handle section 205 (see FIG. 5). If a small element of the patient's tissue 800 has been hooked by manipulation of lip 214, application of tip distal end 216 of laser member 228 allows extremely precise contact with the tissue 800. Then, if tip 216 is of a type heated by laser energy or otherwise, a very precise controlled application of laser-powered energy to a selected portion of the grasped tissue 800 becomes possible. Since the tissue 800 is stretched across the hollow inside of hooked element 208, and tip 216 physically presses thereon, in addition to heating provided by energy delivered through tip 216, there can also be provided an optional application of mechanical force to the tissue 800. See FIG. 8. In other words, the incision, cauterization, or other surgical operation performed on hooked tissue 800 can involve either or both of a mechanical force and a high temperature application of energy. Thus, multiple functions can be performed with the surgical tool in a very precise manner, e.g., a leaking blood vessel can be compressed mechanically, and then sealed when the laser tip is activated.

It is likely that the surgeon may place another, perhaps conventional, cannula with an optic fiber system hooked to a camera or other viewing apparatus above or to the side but very close to the surgical site. This would allow the surgeon to observe which elements of tissue are being hooked for precise surgery.

As best understood with reference to FIG. 9, which may be considered a somewhat enlarged view of the distal end portion per FIG. 3, shaped tip 216 of laser element 228 can be projected through opening 210 of hook element 208. Such a laser element 228 may be of a known type which facilitates optical lighting and/or viewing of tissue not yet approached by opening 210. Thus, in a simple step-by-step, relatively quick and very flexible technique, a surgeon can selectively view, hook, and by the application of high temperature heat incise relatively small amounts of tissue. Note that if the external diameter of cannula 202 is selected to be about 0.5 cm, an external diameter of trocar 218 may be of the order of 3 mm less if it is inserted through a sleeve or if just the shaped tip 216 is selectively formed to be of relatively small diameter. Such small dimensions, and the inherent strength of a tubular metal structure such as the elongate body of cannula 202, provide very small dimensioned but relatively strong and durable guides by which a relatively fragile laser energy transmitting element can be precisely manipulated for access to very confined sites in the patient's body.

In the preferred embodiment, in order to apply a high temperature energy flux to selected tissue hooked by hook element 208 as described above, the elongate laser element 228 is provided an elongate cylindrical, laser light transmitting, body. This body receives a flux of laser energy through an optic fiber 226, through a strain relief element 224, and conveys it to shaped tip portion 216 to deliver the energy to selected tissue.

Tip portion 216 may be made as a discrete element, of a material different from that used to form the elongate main body portion of the laser element 228. Such a tip element can be manufactured in a wide range of shapes and sizes, particularly for the energy-delivering surfaces. The other end of such a tip element may be connected to an energy-delivering end of an optic fiber.

To reduce Fresnel losses at such a junction between an optic fiber and a tip element, the tip element can be provided with a non-abruptly varying reflective index material at its energy-receiving end, as taught in U.S. Pat. No. 5,164,945 to Long et al. Relevant portions of this reference, describing the manner in which such a non-abruptly varying reflective index material distribution may be generated in a tip element are expressly incorporated herein by reference.

The energy-delivering surface of such a tip element may have a small energy-emitting end surface through which laser energy conveyed through the optic fiber may be emitted frontally to cause vaporization of tissue receiving the same. An exemplary tip element of this type is discussed in U.S. Pat. No. 5,164,945, and relevant description thereof is incorporated herein by reference.

Another alternative is to provide a portion of the energy-delivering surface of a tip element as discussed above with a material selected to substantially totally absorb all laser energy received thereat for immediate conversion thereof into thermal energy applicable to tissue by direct contact with an external surface. U.S. Pat. No. 5,164,945 teaches how such a laser energy absorbing material may be ballistically-alloyed to the tip element itself to form a very secure, non-delaminating region in which received laser energy is converted to thermal energy. The manner in which this can be accomplished is also described in this patent and is also expressly incorporated by reference herein.

Figure 10A:
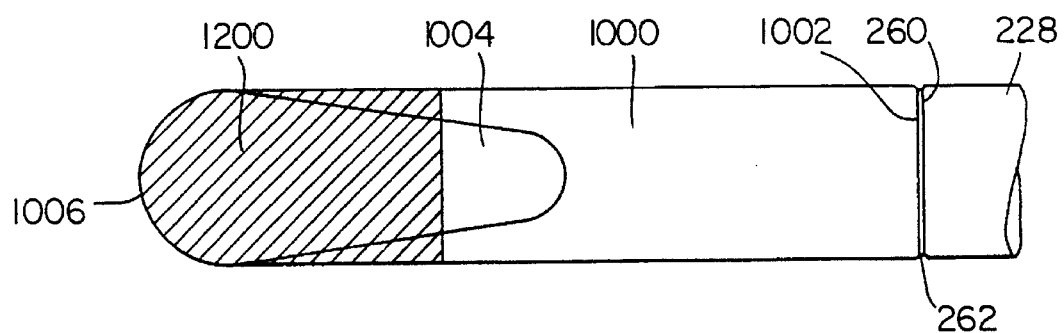
FIGS. 10(A) and 10(B) are two mutually orthogonal side elevation views of one form of a laser energy utilizing tip element for performing incisions and coagulating body fluids when incorporated into the preferred embodiment.
Figure 10B:
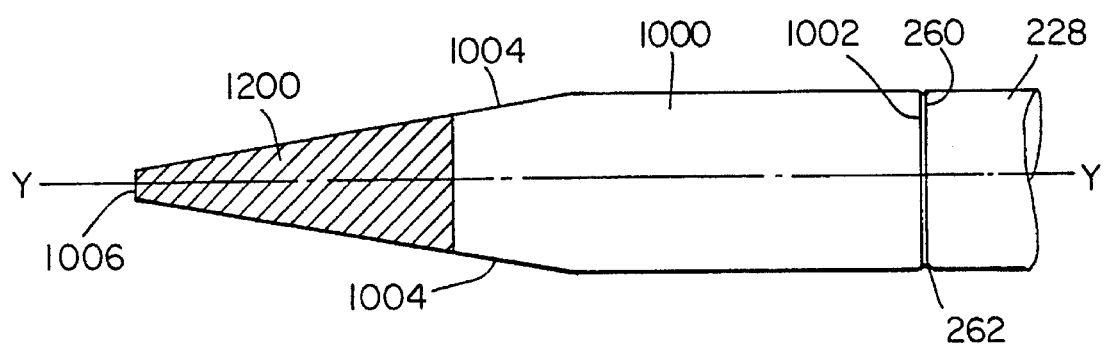

As noted, the tip element may have a variety of shapes and sizes to suit particular needs. Referring to FIGS. 10(a) and 10(B), there is seen an exemplary rounded chisel-like tip element for receiving laser energy through a laser energy transmitting element 218. As illustrated in FIGS. 10(A) and 10(B), such a laser energy transmitting laser element 228 has a body with an end face 260 to which is adhered a thin layer 262 of a known laser-light transmitting adhesive 262. The illustrated exemplary tip element 1000 has a cylindrical body portion with an end surface 1002 adhered by adhesive 262 to end surface 260 of laser member element 218. The energy-delivering end portion of tip element 1000 is provided with two angled flat surfaces 1004,1004, which need not be necessarily symmetric with respect to longitudinal axis Y—Y. In the preferred embodiment, the forwardmost end of tip element 1000 is rounded at a surface 1006, although this also is not mandatory.

Figure 11:
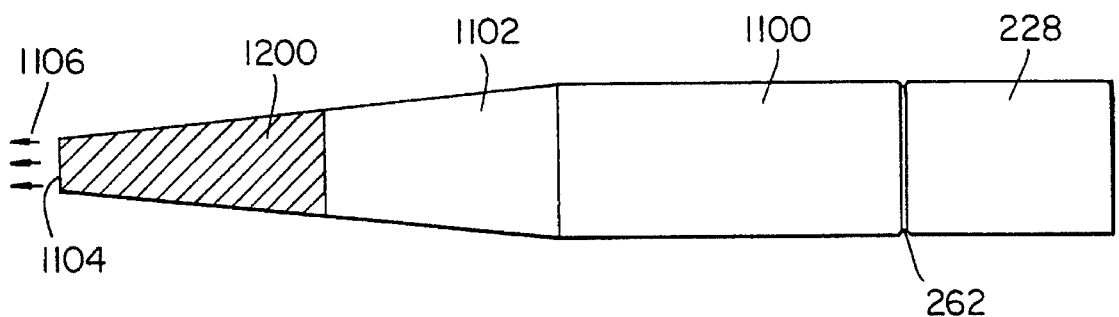
FIG. 11 is a side elevation view of another form of a laser energy utilizing tip element suitable for incorporation into the preferred embodiment.

FIG. 11 illustrates another example of a shape for tip element 1100, of which an energy-delivering portion 1102 is conically shaped. The extreme distal end face 1104 of such a tip element may be used to emit a flux of laser energy forwardly for vaporization of tissue receiving the same, as described above.

With either of the shapes, namely the one illustrated in FIGS. 10(A) and 10(B) or the one illustrated in FIG. 11, the portion of the forwardmost end of the respective tip elements 1000 and 1100 may be provided with the laser energy absorbing material as fully described in U.S. Pat. No. 5,164,945 incorporated herein by reference for its relevant teaching of how such a material may be selected, ballistically-alloyed into the tip element material, and used.

Very briefly, laser light energy received from, for example, the elongate body of laser element 228, per FIG. 10(A), is conveyed through tip element 1000 until it reaches the material 1200, upon which the laser energy received thereat is substantially converted into thermal energy. This results in a very high temperature at the external surface where the laser energy absorbing material 1200 is provided. With the structure according to FIG. 11, a certain portion of laser light energy may be emitted from forward surface 1104, as indicated by the short arrows 1106, while another portion of the laser energy received at the material 1200 would be converted to thermal energy to heat the exposed surface thereof. Such a tip element could thus be used to incise tissue by forward projection of an emitted flux of laser energy, while enabling the application of thermal energy by contacting tissue with the conical portion which contains laser energy absorbing material 1200.

As described in U.S. Pat. 5,164,945, a suitable laser energy absorbing material 1200 is tungsten which absorbs not only the visible portion of the electromagnetic spectrum but also the infrared portion, and has a very high temperature melting point. Other suitable high temperature melting point materials include gold, copper, manganese, beryllium, silicon, iron, platinum, vanadium, rhodium, iridium, niobium, osmium, cobalt, uranium, titanium, chromium, nickel, zirconium, molybdenum, tantalum, yttria, zirconia and alumina. The melting point temperatures of these materials are all greater than 1000° C. Persons of ordinary skill in the art, upon understanding the teaching of U.S. Pat. No. 5,164,945, should be able to select the material, tip element shape, and other structural features to suit specific needs. Accordingly, details of this nature are omitted herein for conciseness.

The present invention is intended to provide a multifunction surgical tool, and one such function is the provision of a cauterization current by the surgeon to immediately cauterize incised blood vessels to prevent continued bleeding therefrom.

Since the hooked element 208 and the cylindrical body of cannula 202 may both be made of an electrically conducting metal, provision of a cauterizing electric current to hooked element may be used to effect cauterizing contact by the external surface thereof pressed to tissue to be cauterized.

FIG. 11 illustrates another exemplary shape for a tip element, in which is included a cylindrical portion 1100 contiguous with a conical portion 1102. A laser energy absorbing material 1200 is provided, as described earlier, at a distal end portion of the conical surface. In the embodiment per FIG. 11, the extreme end face 1104 is not provided the laser energy absorbing material, hence a portion of the laser energy that reaches the tip element is emitted as indicated by arrows 1106. Another portion of the laser energy reaching the conical portion 1102 is absorbed by the material 1200 and converted to heat available at a high temperature for use as described above. With the use of such a tip element, the surgeon can perform very fine incisions on hooked tissue with the forwardly emitted laser energy flux and may thereafter further project and apply the conical heated surface to cauterize the incised tissue.

Figure 12:
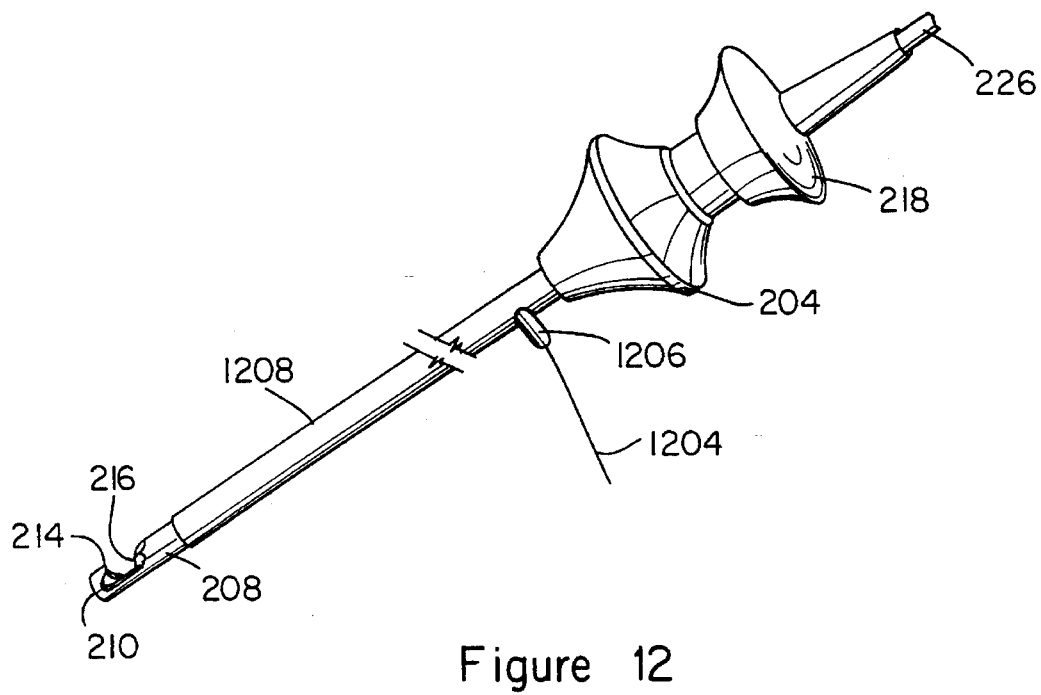
FIG. 12 is a perspective view of another embodiment of the invention which includes an electrocautery function.

In yet another embodiment, per FIG. 12, there is provided a built-in facility for also applying what is commonly known as "electrocauterization" with this invention. In this structure an electrical current-carrying element 1204 is attached to the hook 208 to convey a cauterizing electrical current thereto. A second end of electrical conductor 1204 may be passed through the cylindrical wall of cannula 202 at, for example, a junction 1206, as best seen in FIG. 12, and connected to a source of direct electric current/voltage. A small amount of play may be provided to the length of conductor 1204 to avoid restricting the surgeon in his or her activity.

A thin electrically insulating layer 1208 is provided at the outside surface of cannula 202, preferably all the way to and just past the junction thereof with hooked element 208, to avoid any stray or uncontrolled electrical currents leaking to the tissue of the patient during use of the device. This insulating layer 1208 ensures the non-insulated hooked element 208 receives the current only via insulated body 202 of the cannula.

Figure 13:
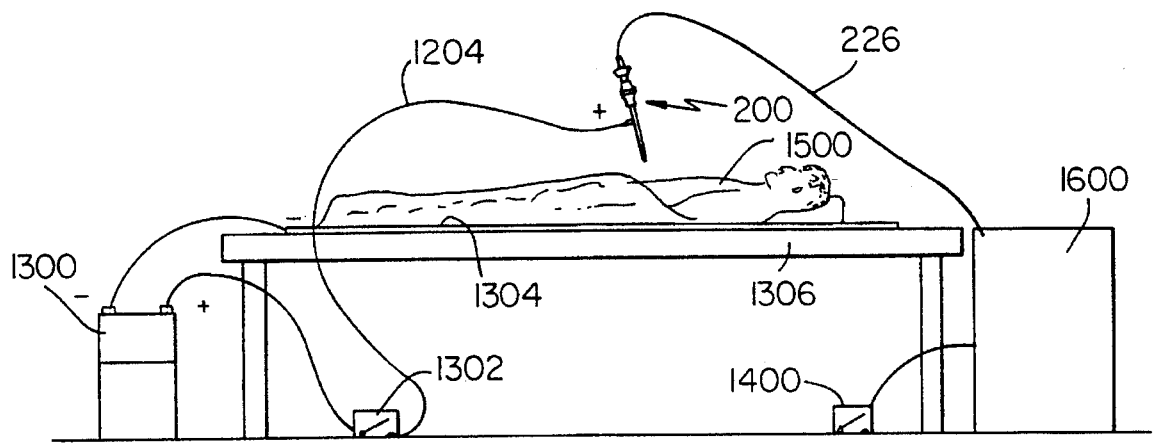
FIG. 13 is a side elevation schematic view of an operating arrangement to enable use of the embodiment per FIG. 11 to perform electrocautery in addition to surgery.

FIG. 13 illustrates a simple, exemplary system for providing the needed electrical cauterizing current. In this system, a battery or other direct electrical current source of suitable voltage 1300 has one terminal, e.g., the positive terminal, connected to a foot-operated switch 1302 which is connected to electrical conductor 1204, and thus to hooked element 208 or to electrically conductive layer 1202 on tip element 1100. The patient 1500 lies in electrical contact with an electrically conductive pad 1304 on a surgical table 1306. Electrically conductive pad 1304 is connected to the second terminal of direct current source 1300. To the surgical tool 1600 is attached via optical fiber 226 a source 1600 of laser energy. Laser source 1600 may be operable by a user-actuated switch or control which may be mounted to the laser element 228 (in known manner, not shown). In the alternative, the surgeon could be seated upon a comfortable seat and be able to access electrical foot switch 1302 with one foot and a second foot-operated switch 1400 connected to actuate laser source 1600 with his or her other foot to deliver laser energy to the tip element 1100.

As will be readily appreciated, the system described above can be used for homeostatic insertion into the patient's body. By heating of the external tissue, by laser-powered energy applied via the trocar tip element and by cauterization to seal off any vessels incised thereby, the surgeon can easily penetrate the device to the surgical site in place of a standard trocar.

By the structures described in the immediately preceding paragraphs, a surgeon familiar with devices including cannulas and cooperating trocars may, with the benefits of the present invention, very precisely hook, i.e, deliberately hold in one place, a small amount of a patient's tissue, then emit laser energy directly thereat to incise it, or apply a heated surface powered by laser energy to vaporize the contacted tissue. He or she may then selectively apply a cauterizing current to stanch any undesirable bleeding thereat. The cannula portion of the present invention may be left in place after such a multifunction operational use of the device, and a known type of optical-observation facilitating trocar may be inserted through the same cannula to optically review in detail the results of the surgical operations just performed. The device may also be inserted through a standard cannula. In the alternative, a second viewing cannula may be used cooperatively.

The present invention has the advantage that all the major mechanical structural elements are of generally well-known geometry and basic structure. The modifications thereto, according to the present invention, need not add significantly add to the cost of such elements, need not affect the general surgical techniques with which most surgeons are familiar, and do not significantly alter the geometries, sizes or costs of the basic elements. U.S. Pat. No. 5,164,945, incorporated herein for its teaching of various specifically-identified aspects, provides the basis for enabling persons of ordinary skill in the art to modify the well-known basic elements to generate the laser energy absorbing surfaces, the electrically-conductive cauterizing layer, and the like. Finally, the hook element 208, in cooperation with the cannula and tip element as taught herein, facilitates precise multifunction surgical operations in highly confined sites in a patient's body without the requirement for major cutting through outer layers of body tissue. The benefits to the patient are obvious: relatively minor external incisions and hence significantly reduced likelihood of infection and complications, fast healing of the outside wound where the device penetrates into the patient's body, clean and antiseptic multiple surgical functions performed quickly and with immediate cauterization of any incidentally severed blood vessels, the consequential reduction in time taken to recover, and lower costs and lost income.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. A multifunction surgical tool for applying a flow of laser-powered energy obtained from a known laser energy source to selected tissue in a patient's body, comprising:

a first element, including an elongate hollow cylindrical body having a first connector part at a first end and a hollow, open, hooked element at a second end, for providing a passage enabling precise access to the selected tissue upon placement of the hooked element inside the patient's body to hook the selected tissue; and a second element, including an elongate element slidably inserted inside the hollow body of the first element, said second element having a second connector part at a connectable end for connection with the first connector part in a manner which permits slidable motion between the first and second connector parts as well as between the first and second elements, the elongate element having a distal end for precisely directed delivery of said flow of laser-powered energy therethrough to the tissue hooked by the hooked element, wherein said first and second connector parts comprise cooperating releasable engagement means which ensure a predetermined limit to the sliding motion therebetween, said limit being selected such that the first and second connector parts have a fully apart position in which the distal end of the elongate element of the first element is inside the elongate part of the second element and a least apart position in which the first and second connector parts are positioned such that the distal end of the elongate part of the second element projects past the open hooked element of the first element and is locked into a locked position relative thereto.

2. The multifunction surgical tool according to claim 1, further comprising:

biasing means cooperating with the first and second connector parts for providing a biasing force directed to bias the first and second connector parts slidably apart when the first and second connector parts are connected to each other, and wherein the first and second connector parts are formed to also permit relative rotational motion unrestricted by the biasing means.

3. The multifunction surgical tool according to claim 2, further comprising:

means for providing a controlled flow of laser energy source for providing a controlled flow of laser energy therefrom to said elongate element for conveyance therethrough to said distal end.

4. The multifunction surgical tool according to claim 1, further comprising:

means cooperating with the known laser energy source for providing a controlled flow of laser energy therefrom to said elongate element for conveyance therethrough to said distal end.

5. The multifunction surgical tool according to claim 1, wherein:

said first element comprises an energy-delivering tip element provided at said distal end of said elongate element to deliver the flow of laser-powered energy to the selected tissue.

6. The multifunction surgical tool according to claim 5, wherein:

said energy-delivering tip element comprises a laser-energy transmitting core portion provided with an energy-delivering external surface from which a directed flow of laser energy is applied to the selected tissue.

7. The multifunction surgical tool according to claim 5, wherein:

said energy-delivering tip element comprises a laser energy transmitting core portion and, in a surface region of said core portion a quantity of laser-energy absorbing material for absorbing laser energy received at said surface region and converting said received laser energy to thermal energy to heat an energy-delivering surface of said surface region.

8. The multifunction surgical tool according to claim 7, wherein:

said laser-energy absorbing material is ballistically-alloyed into said surface region of said energy-delivering tip element so as to be securely bonded therein.

9. The multifunction surgical tool according to claim 8, wherein:

said laser-energy absorbing material is selected from a group of materials consisting of gold, copper, manganese, beryllium, silicon, iron, platinum, vanadium, rhodium, iridium, niobium, osmium, cobalt, uranium, titanium, chromium, nickel, zirconium, molybdenum, tantalum, yttria, zirconia and alumina.

10. A surgical tool for applying a controlled energy flux to selectively engaged tissue in a patient's body, comprising:

an elongate hollow first element having a first connector part at a first end and a hollow, open, hook element at a second end to hook and engage with selected tissue;

an energy-conveying elongate second element slidably and rotatably guided inside the first element, having at a first end a second connector part slidably and rotatably connected to the first connector part and having at a distal second end an energy-delivering surface cooperating with said hook element to apply a controlled flux of energy to incise the engaged tissue; and means for providing an electrical current via said first element to the cauterizing surface of the hook element to cauterize tissue contacted thereby, wherein said first element and said hook element each comprise an electrically conductive material and are in electrically conductive communication, and said hook element has an exterior cauterizing surface.

11. The multifunction surgical tool according to claim 10, further comprising:

biasing means cooperating with the first and second connector parts for slidably biasing apart the first connector part relative to the second connector part, whereby a user-applied force sufficient to overcome the biasing force provided by said biasing means enables sliding movement of the elongate second element through said open hook of the first element.

12. The multifunction surgical tool according to claim 11, wherein:

said second element comprises an energy-delivering tip element provided at said distal second end so as to comprise said energy-delivering surface thereof.

13. The multifunction surgical tool according to claim 12, wherein:

said second element and said tip element each comprise cooperating laser energy transmitting cores; and said tip element comprises a surface region including said energy-delivering surface, said surface region comprising an implanted laser-energy absorbing material for absorbing laser energy conveyed thereto via said second element and tip element cores and converting the conveyed laser energy to thermal energy to heat said energy-delivering surface.

14. The multifunction surgical tool according to claim 13, wherein:

said laser-energy absorbing material is selected from a group of materials consisting of gold, copper, manganese, beryllium, silicon, iron, platinum, vanadium, rhodium, iridium, niobium, osmium, cobalt, uranium, titanium, chromium, nickel, zirconium, molybdenum, tantalum, yttria, zirconia and alumina.

15. The multifunction surgical tool according to claim 14, further comprising:

an electrically insulating material insulating an outside surface of the first element while leaving the cauterizing surface uninsulated.

16. A method for performing surgical operations on selected tissue at a confined internal site in a patient's body, comprising the steps of:

providing an elongate tubular first element having a first connector part at an outside end and an open, hollow, hooked portion at a distal end with the hooked portion engaging the selected tissue;

providing an elongate laser-energy transmitting second element through the tubular first element, With the second element having a second connector at an outside end slidably connected with the first connector and with an energy-delivering tip element at a distal end of the second element located in the open hooked portion of the first element;

slidably moving the tip element relative to the hooked portion, by slidably moving the first and second connector parts relative to each other outside the patient's body, until an energy-delivering surface of the tip element contacts the engaged tissue;

providing a controlled flow of laser energy to the tip element to heat said engaged tissue contacted thereby;

providing a cauterizing surface on said hooked portion of the first element; and providing a controlled electric current to the cauterizing surface for cauterization of tissue contacted by the cauterizing surface.

17. A method for performing surgical operations on selected tissue at a confined internal site in a patient's body, comprising the steps of:

providing an elongate tubular first element having a first connector part at an outside end and an open, hollow, hooked portion at a distal end with the hooked portion engaging the selected tissue;

providing an elongate laser-energy transmitting second element through the tubular first element, with the second element having a second connector at an outside end slidably connected with the first connector and with an energy delivering tip element at a distal end of the second element located in the open hooked portion of the first element;

slidably moving the tip element relative to the hooked portion, by slidably moving the first and second connector parts relative to each other outside the patient's body, until energy-delivering surface of the tip element contacts the engaged tissue;

providing a controlled flow of laser energy to the tip element to heat said engaged tissue contacted thereby;

providing an electrically-conducting surface at said hooked element; and providing a controlled electric current to the electrically-conducting surface for application thereof to tissue to cauterize the same.

18. A method for performing surgical operations on selected tissue at a confined internal site in a patient's body, comprising the steps of:

providing an elongate tubular first element having a first connector part at an outside end and an open, hollow, hooked portion at a distal end with the hooked portion engaging the selected tissue;

providing an elongate laser-energy transmitting second element through the tubular first element, with the second element having a second connector at an outside end slidably connected with the first connector and with an energy-delivering tip element at a distal end of the second element located in the open hooked portion of the first element;

slidably moving the tip element relative to the hooked portion, by slidably moving the first and second connector parts relative to each other outside the patient's body, until an energy-delivering surface of the tip element contacts the engaged tissue;

providing a controlled flow of laser energy to the tip element to heat said engaged tissue contacted thereby;

providing a controlled flow of laser energy to deliver the same as laser-energy emission from the energy-delivering surface of the tip element to heat the engaged tissue;

providing an electrically-conducting layer at said hooked portion of the first element; and providing a controlled electric current to the electrically-conducting layer for application thereof to the engaged tissue to cauterize the same.

19. A method for performing surgical operations on selected tissue at a confined internal site in a patient's body, comprising the steps of:

providing an elongate tubular first element having a first connector part at an outside end and an open, hollow, hooked portion at a distal end with the hooked portion engaging the selected tissue;

providing an elongate laser-energy transmitting second element through the tubular first element, with the second element having a second connector at an outside end slidably connected with the first connector and with an energy-delivering tip element at a distal end of the second element located in the open hooked portion of the first element;

sliddably moving the tip element relative to the hooked portion, by slidably moving the first and second connector parts relative to each other outside the patient's body, until an energy-delivering surface of the tip element contacts the engaged tissue;

providing a controlled flow of laser energy to the tip element to heat said engaged tissue contacted thereby;

providing a controlled flow of laser energy to an energy-converting surface region under said energy-delivering surface of the tip element, and converting the laser energy into thermal energy to heat the surface region for application of a thermal energy flux thereby by contacting the engaged tissue;

providing an electrically-conducting layer at said hooked portion of the first element; and providing a controlled electric current to the electrically-conducting layer for application thereof to the engaged tissue to cauterize the same.

* * * * *